(12) United States Patent
Dong et al.

(10) Patent No.: US 9,005,608 B2
(45) Date of Patent: Apr. 14, 2015

(54) STABILIZED SOLUBILITY-ENHANCED FORMULATIONS FOR ORAL DELIVERY

(75) Inventors: Liang C. Dong, Sunnyvale, CA (US); Katrina Andrea U. Co, St. Martinez, CA (US); Shu Li, Union City, CA (US); Crystal Pollock-Dove, Mountain View, CA (US)

(73) Assignee: Adds Pharmaceuticals LLC, Sunnyvale, CA (US)

( * ) Notice: Subject to any disclaimer, the term of this patent is extended or adjusted under 35 U.S.C. 154(b) by 684 days.

(21) Appl. No.: 12/730,944

(22) Filed: Mar. 24, 2010

(65) Prior Publication Data

US 2010/0247632 A1 Sep. 30, 2010

Related U.S. Application Data

(60) Provisional application No. 61/297,643, filed on Jan. 22, 2010, provisional application No. 61/162,990, filed on Mar. 24, 2009.

(51) Int. Cl.

| | |
|---|---|
| A61K 38/43 | (2006.01) |
| A61K 9/00 | (2006.01) |
| A61K 9/20 | (2006.01) |
| A61K 9/48 | (2006.01) |
| A23L 1/30 | (2006.01) |
| A23L 1/302 | (2006.01) |
| A23L 1/303 | (2006.01) |
| A61K 9/107 | (2006.01) |
| A61K 9/24 | (2006.01) |

(52) U.S. Cl.
CPC .......... *A61K 9/4858* (2013.01); *A23L 1/30* (2013.01); *A23L 1/3002* (2013.01); *A23L 1/302* (2013.01); *A23L 1/303* (2013.01); *A61K 9/107* (2013.01); *A61K 9/2054* (2013.01); *A61K 9/209* (2013.01)

(58) Field of Classification Search
USPC .......................................... 424/94.1, 400, 465
See application file for complete search history.

(56) References Cited

U.S. PATENT DOCUMENTS

| | | | |
|---|---|---|---|
| 4,483,873 A | 11/1984 | Ohashi et al. | |
| 6,045,826 A | 4/2000 | Borowy-Borowski et al. | |
| 6,056,971 A | 5/2000 | Goldman | |
| 6,087,386 A | 7/2000 | Chen et al. | |
| 6,300,377 B1 | 10/2001 | Chopra | |
| 6,417,233 B1 * | 7/2002 | Sears et al. .................... | 514/549 |
| 6,441,050 B1 | 8/2002 | Chopra | |
| 7,030,155 B2 * | 4/2006 | Lambert et al. ............... | 514/449 |
| 7,094,804 B2 | 8/2006 | Behnam | |
| 7,273,624 B2 | 9/2007 | Rosenberg et al. | |
| 7,438,903 B2 | 10/2008 | Parkhideh | |
| 2003/0065024 A1 | 4/2003 | Lambert et al. | |
| 2004/0247539 A1 * | 12/2004 | Wendel et al. ................. | 424/59 |
| 2005/0008581 A1 * | 1/2005 | Parkhideh ....................... | 424/46 |
| 2005/0207990 A1 | 9/2005 | Funke et al. | |
| 2006/0051462 A1 * | 3/2006 | Wang .............................. | 426/72 |

FOREIGN PATENT DOCUMENTS

| | | |
|---|---|---|
| WO | WO-00/38655 | 7/2000 |
| WO | WO-2005/111224 | 11/2005 |

OTHER PUBLICATIONS

International Search Report and Written Opinion for PCT/US10/25812, mailed May 4, 2010, 6 pages.

* cited by examiner

*Primary Examiner* — Blessing M Fubara
*Assistant Examiner* — Jennifer A Berrios
(74) *Attorney, Agent, or Firm* — Morrison & Foerster LLP

(57) ABSTRACT

Methods and compositions are described whereby poorly water-soluble beneficial agents such as vitamins and co-factors are formulated into self-emulsifying formulas (SEF) and optionally sorbing the SEF into pores of porous solid particulates, or preparing supersaturated solutions (SSS) and sorbing the SSS into pores of porous solid particulates. These formulations are useful as dosage forms with oral availability.

8 Claims, 1 Drawing Sheet

CoQ10 Dissolution Profiles for Various Commercial Products

Only can AQUA Q10 satisfy USP criterion (75% of label dissolved in one hr.) as Water-soluble $CoQ_{10}$

Model Prediction Shows the Sweet Zone (> 85% CoQ10 dissolved)

STABILIZED SOLUBILITY-ENHANCED FORMULATIONS FOR ORAL DELIVERY

CROSS-REFERENCE TO RELATED APPLICATIONS

This application claims priority from U.S. provisional applications 61/162,990, filed 24 Mar. 2009, and 61/297,643, filed 22 Jan. 2010. The contents of these documents are incorporated herein by reference.

TECHNICAL FIELD

The present invention relates to enhancing oral bioavailability for poorly water-soluble beneficial agents. More particularly, the invention relates to compositions that incorporate super-saturated solutions or self-emulsifying formulations of such agents into the pores of a porous solid particulate, or compositions that are said self-emulsifying formulations alone.

BACKGROUND ART

Lipophilic molecules, such as nutrients and vitamins, are poorly solubilized in the aqueous medium along the gastrointestinal tract, thereby leading to poor bioavailability. These nutrients, including Coenzyme Q10, vitamins A, D, E and K, lycopene, lutein, resveratrol, and others, are not readily absorbed by body due to this poor solubility in an aqueous medium, i.e., the gastrointestinal fluid. The compromised bioavailability of these nutrients would be mitigated by solubility-enhancing technologies that can increase their bioavailability and efficacy. Various attempts have been made to solve this problem.

For example, U.S. Pat. No. 6,045,826 discloses water-soluble compositions containing a lipophilic compound (including $CoQ_{10}$) and a single solubilizing agent having both hydrophobic and hydrophilic moieties.

Formulations useful for delivery of a particular exemplary beneficial agent, coenzyme Q ($CoQ_{10}$) are described in the art. U.S. Pat. No. 7,438,903 notes that softgels are the most popular method of $CoQ_{10}$ delivery, and $CoQ_{10}$ is available commercially in the form of tablets, hard capsules and softgel capsules either alone or in combination with other vitamins and/or supplements. U.S. Pat. No. 4,483,873 discloses aqueous solutions of $CoQ_{10}$ that contain hydrogenated lecithin putatively to increase $CoQ_{10}$ bioavailability. U.S. Pat. Nos. 6,056,971, 6,441,050 and 7,094,804 disclose methods for solubilizing water-insoluble dietary supplements in liquid form, such as $CoQ_{10}$ in a softgel, by mixing $CoQ_{10}$ with, among other things, an edible polyhydric alcohol solvent. U.S. Pat. No. 6,300,377 teaches the formulation of a $CoQ_{10}$ composition that omits polyhydric alcohol, but includes other agents to help improve solubility, including a glyceryl ester molecule having one to three $C_2$-$C_7$ acyl groups. WO/2005/111224 discloses $CoQ_{10}$ complexes with beta-cyclodextrin to increase $CoQ_{10}$ solubility in water.

U.S. Pat. No. 7,273,624 describes a melt extrusion process to prepare a $CoQ_{10}$ solid dispersion in a matrix-forming excipient. U.S. Pat. No. 7,438,903 discloses $CoQ_{10}$ nanocrystals dispersed in lipid-based carriers.

WO 00/38655A-1 describes formulations comprising porous calcium hydrogen phosphate particulates, sold commercially under the trademark Fujicalin®, within which a liquid formulation of an active agent is absorbed, so that the liquid-absorbing particulates can be processed using conventional pharmaceutical equipment. These formulations are said to provide high concentrations of active drug dosage without loss of active pharmaceutical agent during the manufacturing process, and to permit delivery of active pharmaceutical agent, along with suitable solubilization-enhancers to the absorption site. Other forms of the porous particulates are also disclosed including microcrystalline cellulose, silicon dioxide, or magnesium aluminosilicate, or blends thereof. However, this publication does not disclose incorporation of a supersaturated solution (SSS) of drug or a self-emulsifying formulation (SEF) of a drug so as to prevent reprecipitation.

DISCLOSURE OF THE INVENTION

The invention provides compositions and methods whereby poorly water-soluble beneficial agents, such as vitamins and co-factors, demonstrate improved bioavailability through enhancing their solubility in luminal fluid of the gastrointestinal tract. In one embodiment, this is accomplished by providing a super-saturated solution (SSS) using elevated temperatures or a self-emulsifying formulation (SEF), also using elevated temperatures and sorbing the SSS or SEF into the pores of a porous particulate with sufficiently small pores to prevent the agent from re-precipitating or re-crystallizing during storage. These solid forms may be included in capsules or formed into tablets. The SEF formulations themselves may also be used, including when contained in capsules.

Thus, in one aspect, the invention is directed to a dosage form designed for oral administration which comprises a super-saturated solution of, or a self-emulsifying formulation of, a poorly water-soluble beneficial agent which is sorbed into the pores of a solid porous particulate, wherein said pores are sufficiently small to prevent the agent from re-precipitating or re-crystallizing, or wherein the dosage form comprises a self-emulsifying formulation per se.

In another aspect, the invention is directed to methods to prepare these formulations which methods comprise preparing an SSS or SEF of the one or more poorly water-soluble beneficial agents at a first temperature above room temperature, sorbing the SSS or SEF at this temperature into the pores of the particulate porous solid, and then cooling to room temperature or storage temperature, or simply cooling the SEF to room temperature.

In general, the invention provides enhanced bioavailability of poorly-water-soluble beneficial agents, including, but not limited to, lipid-soluble vitamins and vitamin-like substances, to improve their bioavailability.

MODES OF CARRYING OUT THE INVENTION

Figure 1:
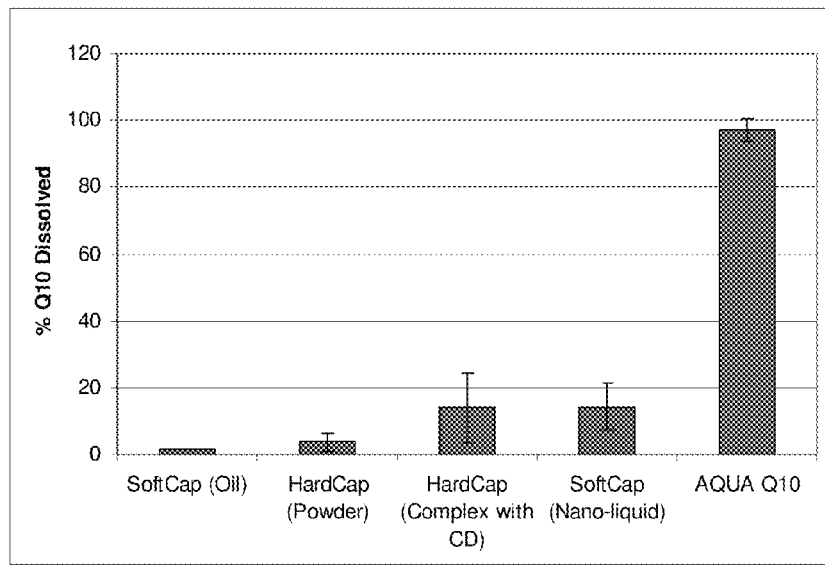
FIG. 1 is a graph showing the comparative ability of the invention formulation to release $CoQ_{10}$ into aqueous solution as compared to commercial formulations of $CoQ_{10}$.

We have found that the solubility of $CoQ_{10}$ in non-aqueous formulations can be greatly increased at an elevated temperature close to its melting temperature (48° C.), with >100 mg/ml being achievable. Surprisingly, we have also discovered that incorporation of the high concentrated solution or emulsion into a porous carrier can prevent $CoQ_{10}$ from re-crystallization when the temperature is reduced to room temperature. While not intending to be bound to any theory, we posit that when a poorly water-soluble agent is incorporated into a porous carrier with narrow pores, it experiences strong geometric restrictions and large interfacial interactions with the porous matrix. This surface energy term is expected to significantly lower the phase transition temperature. Strong geometric restrictions may also inhibit forming of orderly crystalline structure, leading to solubilized form if a solubility-enhancing component is present. Thus, absorbing a previously solubilized $CoQ_{10}$ liquid formulation, for example, into the narrow pore channels of Fujicalin® (calcium hydrogen phosphate) inhibits re-crystallization and aggregation of $CoQ_{10}$. This enables, to a large extent, even dispersion and distribution of pharmaceutically active forms of $CoQ_{10}$ in solubilized form. After the Fujicalin® porous particulates dissolve in acidic gastric fluid, the SSS is released and the trapped SEF self-emulsifies in the fluid to form droplets of sufficiently small size, thereby facilitating absorption of $CoQ_{10}$ cross the epithelial cells. Other porous particulates include silicon dioxide and magnesium aluminum metasilicate. Combinations may also be used.

We have also found that the SEF prepared can be cooled to room temperature and can itself be used as a dosage form.

The invention is also directed to a manufacturing process to load high amounts of beneficial agents in solubilized form while allowing for excellent distributive mixing of the agent in an oral solid dosage form. All these allow for the commercialization of a viable product with enhanced oral bioavailability. The compositions and methods of the invention improve oral bioavailability of poorly water-soluble beneficial agents such as $CoQ_{10}$, Vitamin A, Vitamin D, Vitamin E and Vitamin K, lycopene, lutein, resveratrol, Ginseng extract, curcumin, saw palmetto lipid extract, echinacea extract, hawthorne berry extract, lipoic acid, kava extract, hypericum, quercitin extract and the like, as well as combinations thereof. A non-limiting list of appropriate beneficial agents is included below.

In one embodiment, a super-saturated solution (SSS) is prepared by mixing the agent with a suitable polymer surfactant such as polyethylene glycol/polypropylene glycol copolymers and a volatile liquid such as an alcohol. The solution is made super-saturated by heating to an elevated temperature which is above room temperature and close to its melting temperature, typically in the range of 45 to 65° C. or any specific temperature in this range, such as 48° C. or 50° C. and then sorbing the super-saturated solution into the pores of a suitable particulate porous solid with pore size sufficiently small to prevent re-precipitation of the agent when the solvent is evaporated and the particulate sorbent is cooled to storage temperatures. Storage temperatures can be room temperature and below.

Alternatively, the invention employs self-emulsifying formulations (SEF) optionally for sorption into the pores of the porous particulates. In this embodiment, the SEF comprises an effective amount of agent, a water soluble, non-ionic surfactant and at least one lipid-soluble component. The formulation causes the agent readily to self-emulsify in an aqueous medium to become an oil-in-water emulsion, thereby leading to enhanced absorption cross the epithelial cells lining along the gastrointestinal tract. The oil-in-water emulsion may have oil droplet sizes less than 0.45 µm. The SEF is prepared at similar elevated temperatures, optionally sorbed into the porous particulates and then cooled. Thus, the invention compositions include both SEF which is used directly or incorporated into capsules and SEF which is sorbed onto pores of porous particulates.

The water-soluble, non-ionic surfactant for the SEF may be, for example, Vitamin E TPGS, Polysorbate 80™, polyoxyl 35 castor oil or Solutol® HS-15. The lipid-soluble component may be any of omega-3 fatty acids, other unsaturated fatty acids, acetated mono-glyceride, mono-, di-, tri-glycerides, propylene monoglyceride, or their mixtures. The omega-3 fatty acids may include, for example, alpha-linolenic acid (ALA), eicosapentaenoic acid (EPA), and docosahexaenoic acid (DHA).

The resulting particulates obtained either through the use of SSS or SEF initial formulations can then be provided in a suitable unit dosage form such as a hard or soft capsule or a tablet. For formation of tablets, the particulates are mixed with other excipients including binders, disintegrants and lubricants and pressed into tablets using conventional technology. For formation of capsules, the solid particulates are simply loaded into hard shell capsules, again using standard technology.

In another alternative, the particulates may be dissolved or suspended or otherwise dispersed in liquids to form a liquid formulation. The formulation may also be mixed into food products or into animal feed.

Thus, an agent can be administered to produce a localized or systemic effect or effects in animals, including warm blooded mammals, humans and primates; domestic household or farm animals such as cats, dogs, sheep, goats, cattle, horses and pigs; laboratory animals such as mice, rats and guinea pigs; zoo and wild animals; and the like. The dosage form may be used in dietary, nutraceutical, veterinary or pharmaceutical compositions.

One illustrative beneficial agent that has been successfully formulated according to the invention method is coenzyme $Q_{10}$.

Coenzyme $Q_{10}$ ($CoQ_{10}$), also known as ubiquinone, is the coenzyme for at least three mitochondrial enzymes (complexes I, II and III) as well as enzymes in other parts of the cell. It is largely responsible for transfer of electrons within the oxidative phosphorylation pathway for production of the high-energy adenosine triphosphate (ATP), upon which all cellular functions rely.

In addition to its role as an electron carrier, it serves as an antioxidant. Its structure that allows it to act as an electron-transporter enables it to scavenge free radicals, thus preventing oxidative damage to DNA, lipids, and cellular proteins.

Its presence in the body is affected by its rate of biosynthesis as well as adequate absorption from available dietary sources. Synthesis of $CoQ_{10}$ in the body declines after age 20, and its brain levels fall markedly after age 50. $CoQ_{10}$ deficiency has been observed in many diverse disease pathologies, and is likely to occur within the elderly population. Individuals taking certain cholesterol-lowering drugs, undergoing chemotherapy and AIDS retroviral therapy (which generate significant levels of free radicals and other oxidative stressors in vivo), or having certain genetic defects for mitochondrial proteins may be more susceptible to $CoQ_{10}$ deficiency. Significant deficiency of this essential molecule can also have debilitating health effects.

Striking results have been reported in many patients with cardiovascular disease, cancer and infectious diseases simply by oral supplementation of $CoQ_{10}$. It may also have significant positive impact on individuals with certain neurodegenerative conditions like Huntington's disease and Parkinson's disease. It can be useful in the prevention of hypertension and atherosclerosis, and can improve patient quality of life during recuperation from open-heart surgery. As an excellent antioxidant, it is even believed to help prevent cancer, as well as ameliorate the effects of the aging process.

$CoQ_{10}$ in a concentration of >100 mg/ml in a non-aqueous formulation, preferably SEF, at a temperature above 25° C., preferably at or above 48° C. has been achieved.

The invention discloses manufacturing processes to load high amounts of $CoQ_{10}$ in solubilized form while allowing for excellent distributive mixing of $CoQ_{10}$ in an oral solid dosage form. All these allow for the commercialization of a viable $CoQ_{10}$ product with enhanced oral bioavailability. Similarly, these methods can also improve oral bioavailability of poorly water-soluble nutrients including vitamin A, vitamin D, vitamin E, vitamin K, lycopene, lutein, and others.

The invention formulations solubilize $CoQ_{10}$ at a concentration of >100 mg/ml at a temperature between 30° C. and 60° C., preferably not above 50° C. In addition, the nutrient/vitamin components readily dissolve in aqueous media, so that >75% of these components are released within an hour.

One illustrative embodiment comprises the steps of: (a) dissolving an amount of $CoQ_{10}$ in a Pluronic® F127 solution in isopropyl alcohol (IPA) to form an SSS, (b) loading the SSS into the pores of the calcium hydrogen phosphate particulates, and (c) evaporating IPA to form solution by sorbing the SSS into the pores of the particulates. Steps a) and b) are conducted at elevated temperatures, and the solid particulates having the sorbed SSS in the pores thereof are then cooled to room temperature or below for storage. This can then be blended with other excipients, including a binder, a disintegrate and a lubricant, and compressed into a tablet, or can be loaded into capsules.

In another illustrative embodiment, $CoQ_{10}$ contained in a self-emulsifying formulation (SEF) comprising Vitamin E TPGS and omega-3 fatty acid is prepared. This SEF can emulsify in an aqueous medium, resulting in a stable oil-in-water emulsion, thereby preventing $CoQ_{10}$ from precipitating in the aqueous medium. Thus, the SEF is prepared by: (a) dissolving an amount of $CoQ_{10}$ in a SEF at an elevated temperature, (b) incorporating the $CoQ_{10}$ solution (>100 mg/ml) in the SEF into the pores of the calcium hydrogen phosphate particulates and cooling. If desired, the SEF-loaded particulates may be loaded into a two-piece hard capsule (V-Cap or Quali-V®), or formed into tablets as above.

Another illustrative embodiment provides oral dosage form comprising lipid-soluble vitamins A, D, E and K. This may be prepared by: (a) preparing an SSS by dissolving the lipid-soluble vitamins A, D, E and K in a Pluronic® F127 solution in isopropyl alcohol (IPA) at an elevated temperature, (b) loading the vitamin solution into the pores of the calcium hydrogen phosphate powder, and (c) evaporating IPA to form a solid solution. This can optionally be blended with minerals, water-soluble vitamins and other excipients, including a binder, a disintegrant and a lubricant, and compressed into a tablet, or may be used to fill capsules.

In another illustrative embodiment, a vitamin/mineral composition is provided using a self-emulsifying formulation (SEF) comprising Vitamin E TPGS and omega-3 fatty acid. This SEF can emulsify in an aqueous medium, resulting in a stable oil-in-water emulsion and thereby preventing poorly water-soluble vitamins from precipitating in the aqueous medium. This is prepared by: (a) dissolving the poorly water-soluble vitamins A, D and K in the SEF, and (b) incorporating the vitamin solution into the pores of the calcium hydrogen phosphate particulates. If desired, the SEF-loaded particulates can be blended with minerals, water-soluble vitamins and other excipients, including a binder, a disintegrant and a lubricant, and compressed into a tablet, or may be used to fill capsules.

In another illustrative embodiment, a $CoQ_{10}$ composition is provided using a self-emulsifying formulation (SEF) comprising Vitamin E TPGS and omega-3 fatty acid or Cremophor™ EL and acetated monoglyceride. This SEF can be dispersed in a flavor-containing water to result in a stable drink concentrate with $CoQ_{10}$ concentration>100 mg/ml.

In another illustrative embodiment, a composition of the poorly water-soluble vitamins A, D and K is provided using a self-emulsifying formulation (SEF) comprising Vitamin E TPGS and omega-3 fatty acid or Cremophor™ EL and acetated monoglyceride. This SEF can be dispersed in a flavor-containing water to result in a stable drink concentrate.

In one embodiment, the invention relates to a method for preparing a $CoQ_{10}$/Vitamin E oral dosage form. The method comprises the steps of: (a) dissolving an amount of $CoQ_{10}$ and d,l-α-tocopheryl acetate as vitamin E in a liquid formulation comprising polyoxyl 35 castor oil or Polysorbate 80™, ethyl ester of omega 3-fatty acid and a mono-, di-glyceride, (b) encapsulating the solution of $CoQ_{10}$ and vitamin E with a two-piece hard capsule, preferably hydroxypropylmethylcellulose (HPMC) capsule, and (c) sealing the liquid-filled hard capsule with a mixture of water and ethanol (50/50 by volume) or with a capsule banding machine.

In another embodiment, the invention relates to a method for preparing a $CoQ_{10}$/Vitamin E oral dosage form. The method comprises the steps of: (a) dissolving an amount of $CoQ_{10}$ and d,l-α-tocopheryl acetate as vitamin E in a liquid formulation comprising polyoxyl 35 castor oil or Polysorbate 80™, ethyl ester of omega 3-fatty acid and a mono-, di-glyceride, (b) loading the solution of $CoQ_{10}$ and vitamin E into the pores of the calcium hydrogen phosphate particulates, and (c) filling the SEF-sorbing particulates into a two-piece hard capsule, preferably hydroxypropylmethylcellulose (HPMC) capsule.

In another embodiment, the invention relates to a method for preparing a $CoQ_{10}$/Vitamin E/Vitamin D oral dosage form. The method comprises the steps of:

(a) dissolving an amount of $CoQ_{10}$, d,l-α-tocopheryl acetate as vitamin E and cholecalciferol as vitamin D in a liquid formulation comprising polyoxyl 35 castor oil or Polysorbate 80™, ethyl ester of omega 3-fatty acid and a mono-, di-glyceride, (b) loading the solution of $CoQ_{10}$, vitamin E and vitamin D into the pores of the calcium hydrogen phosphate particulates, (c) dry-blending or granulating the SEF-sorbing particulates with other excipients, including a disintegrate, a lubricant, and a binder (optional), and (d) compressing the blend or granules into a tablet.

In another embodiment, the invention relates to a method for preparing a $CoQ_{10}$/Multi-vitamins oral dosage form for young adults. The method comprises the steps of: (a) dissolving an amount of $CoQ_{10}$, d,l-α-tocopheryl acetate as vitamin E, cholecalciferol as vitamin D, retinol palmitate as vitamin A and 3-phytylmenadione as vitamin K in a liquid formulation comprising polyoxyl 35 castor oil or Polysorbate 80™, ethyl ester of omega 3-fatty acid and a mono-, di-glyceride, (b) loading the solution of $CoQ_{10}$ and vitamins A, D, E and K into the pores of the calcium hydrogen phosphate particulates, (c) dry-blending or granulating the SEF-sorbing particulates with other excipients, including a disintegrate and a lubricant, and a binder (optional), (d) dry-blending or granulating a composition comprising ascorbic acid, calcium D-pantothenate, folic acid, niacinamide, pyridoxine hydrochloride, riboflavin, thiamine mononitrate, cyanocobalamin, copper gluconate, zinc oxide, ferrous fumarate, magnesium phosphate, manganese sulfate, potassium iodide, sodium molybdate, sodium selenite, biotin, potassium chloride, chromium chloride, boron amino acid chelate, nickel sulfate, silicon dioxide, stannous chloride, sodium metavanadate, a disintegrate, a lubricant, and a binder (optional), and (e) compressing these two blends or granules into a bi-layer tablet, with one layer comprising the oil-soluble nutrients, and the other comprising water-soluble vitamins and minerals.

In another embodiment, the invention relates to a method for preparing a $CoQ_{10}$/Multi-vitamins oral dosage form. The method comprises the steps of: (a) dissolving an amount of $CoQ_{10}$, d,l-α-tocopheryl acetate as vitamin E, cholecalciferol as vitamin D, retinol palmitate as vitamin A, 3-phythylmenadione as vitamin K, lycopene and lutein in a liquid formulation comprising polyoxyl 35 castor oil or Polysorbate 80™, ethyl ester of omega 3-fatty acid and a mono-, di-glyceride, (b) loading the solution of $CoQ_{10}$, vitamins A, D, E, K, and lutein into the pores of the calcium hydrogen phosphate particulates, (c) dry-blending or granulating the SEF-sorbing particulates with other excipients, including a disintegrate and a lubricant, and a binder (optional), (d) dry-blending or granulating a composition comprising ascorbic acid, calcium D-pantothenate, folic acid, niacinamide, pyridoxine hydrochloride, riboflavin, thiamine mononitrate, cyanocobalamin, copper gluconate, lycopene, zinc oxide, magnesium phosphate, manganese sulfate, potassium iodide, sodium molybdate, sodium selenite, biotin, potassium chloride, chromium chloride, boron amino acid chelate, nickel sulfate, silicon dioxide, sodium metavanadate, a disintegrate, a lubricant, and a binder (optional), and (e) compressing these two blends or granules into a bi-layer tablet, with one layer comprising the oil-soluble nutrients, and the other comprising water-soluble vitamins and minerals.

In another embodiment, the invention relates to a method for preparing a $CoQ_{10}$, or oil-soluble vitamins or other poorly water-soluble nutrients for pediatric and geriatric application. In addition to the enhanced dissolution of these poorly water-soluble nutrients, the tablet in this embodiment can disintegrate rapidly in the oral cavity, thereby making swallow the normally large supplement tablets much easier.

Suitable beneficial agents may be selected from, for example, vitamins, coenzymes, enzymes, enzyme inhibitors, hormones, proteins, polynucleotides, nucleoproteins, polysaccharides, glycoproteins, lipoproteins, polypeptides, steroids, hypnotics and sedatives, psychic energizers, tranquilizers, anticonvulsants, antidepressants, muscle relaxants, anti-Parkinson's agents, analgesics, anti-inflammatories, antihistamines, local anesthetics, muscle contractants, antimicrobials, antimalarials, antivirals, antibiotics, anti-obesity agents, hormonal agents including contraceptives, sympathomimetics, polypeptides and proteins capable of eliciting physiological effects, diuretics, lipid regulating agents, anti-androgenic agents, antiparasitics, neoplastics, antineoplastics, antihyperglycemics, hypoglycemics, nutritional agents and supplements, growth supplements, fats, ophthalmics, anti-enteritis agents, electrolytes and diagnostic agents.

Examples of particular beneficial agents useful in this invention include ubiquinone ($CoQ_{10}$), ubiquinol, Vitamin A, Vitamin D, Vitamin E, Vitamin K, carvedilol, isotretinoin, dutasteride, finasteride, fentanyl, sufentanyl, zaleplon, risperidone, sumatriptan, prochlorperazine edisylate, ferrous sulfate, albuterol, aminocaproic acid, mecamylamine hydrochloride, procainamide hydrochloride, amphetamine sulfate, methamphetamine hydrochloride, benzphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperazine maleate, anisindione, diphenadione erythrityl tetranitrate, digoxin, isofluorophate, acetazolamide, nifedipine, methazolamide, bendroflumethiazide, chlorpropamide, glipizide, glyburide, gliclazide, tobutamide, chlorproamide, tolazamide, acetohexamide, metformin, troglitazone, orlistat, bupropion, nefazodone, tolazamide, chlormadinone acetate, phenaglycodol, allopurinol, aluminum aspirin, methotrexate, acetyl sulfisoxazole, hydrocortisone, hydrocorticosterone acetate, cortisone acetate, dexamethasone and its derivatives such as betamethasone, triamcinolone, methyltestosterone, 17-β-estradiol, ethinyl estradiol, ethinyl estradiol 3-methyl ether, prednisolone, 17-β-hydroxyprogesterone acetate, 19-norprogesterone, norgestrel, norethindrone, norethisterone, norethiederone, progesterone, norgesterone, norethynodrel, terfandine, fexofenadine, aspirin, acetaminophen, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, selegiline, chlorpromazine, methyldopa, dihydroxyphenylalanine, calcium gluconate, ketoprofen, ibuprofen, cephalexin, erythromycin, haloperidol, zomepirac, ferrous lactate, vincamine, phenoxybenzamine, diltiazem, milrinone, captropril, mandol, quanbenz, hydrochlorothiazide, ranitidine, flurbiprofen, fenbufen, fluprofen, tolmetin, alclofenac, mefenamic, flufenamic, difuninal, nimodipine, nitrendipine, nisoldipine, nicardipine, felodipine, lidoflazine, tiapamil, gallopamil, amlodipine, mioflazine, lisinopril, enalapril, captopril, ramipril, enalaprilat, famotidine, nizatidine, sucralfate, etintidine, tetratolol, minoxidil, chlordiazepoxide, diazepam, amitriptyline, and imipramine, and pharmaceutical salts of these active agents.

The following examples illustrate but do not limit the invention.

Example 1

Standard AQUA SEF

An SEF was prepared from 10% $CoQ_{10}$, 5% vitamin E (d,l-α-tocopheryl acetate), 40.0% omega-3 fatty acid ethyl ester (Incromega™ 3322), 25.0% mono-, di-glycerides of caprylic (optional) acid (Capmul™ CMC C-8), and 20.0% polyoxyl 35 castor oil (Cremophor™ EL) by weight, thus resulting in the "AQUA" formulation of Incromega™ E3322/Capmul™ CMC C-81/Cremophor™ EL at 40/25/20. All the components were mixed for ~5 mins at 50° C. After mixing, $CoQ_{10}$ was completely dissolved, resulting in a clear, orange-colored solution, which was filled into size #2 hydroxypropylmethyl cellulose (HPMC) hard capsules with the target weight of 300 mg SEF/capsule. The capsules were sealed with a mixed solvent of ethanol and de-ionized water at 50/50 by volume. Each capsule thus contains 30 mg of $CoQ_{10}$.

The liquid-filled hard capsules (LFHC) were tested for their ability to release $CoQ_{10}$ into solution in water at 37° C. in 500 ml of de-ionized water, using USP method I (basket) at 75 rpm. After one hour, the dissolution medium was passed through a 0.45 µm-nylon filter, and the $CoQ_{10}$ concentration in the filtrate was measured after dilution with ethanol using an HPLC method. The assay parameters are listed in Table 1 below.

TABLE 1

HPLC Assay Parameters

Instrument

Agilent 1100 Series LC with auto sampler and injector,
Agilent 1100 UV detector
Waters XTerra ® RP18, 3.5 m, 4.6 mm i.d. × 150 mm
Operating parameters Mobile Phase: Acetonitrile/Tetrahydrofuran/Water (55/40/5 v/v/v)
Flow Rate: 1.0 ml/min
Injection Volume: 20 μl
Column Temperature: Ambient
Detector Wavelength: 275 nm Other commercially available $CoQ_{10}$ products were also measured for their dissolution in de-ionized water using this method. These products are various oral dosage forms, including a soft capsule containing a $CoQ_{10}$ suspension in soybean oil, a $CoQ_{10}$ powder in hard capsule, a $CoQ_{10}$ complex with cyclodextrin in a hard capsule and $CoQ_{10}$ nano liquid formulation in soft capsule.

As shown in FIG. 1, the LFHC of this example is superior to these other products. More than 75% of $CoQ_{10}$ dissolved within 1 hr., which satisfies the USP criterion for water-soluble $CoQ_{10}$.

Example 2

Solubility of $CoQ_{10}$ in AQUA $CoQ_{10}$ solubility was measured at 37° C. in water as well as in a placebo AQUA Q10 formulation, i.e., Incromega™ E3322, Capmul™ CMC C-8, and Cremophor™ EL at weight ratio of 40/25/20. $CoQ_{10}$ solubility in AQUA Q10 formulation (177 mg/ml) is over 400,000 times higher than its solubility in water (0.4 μg/ml).

Example 3

Variation of SEF Constituents

In this example, $CoQ_{10}$ and vitamin E acetate were kept constant at 10% and 5% by weight, respectively. The content of other three components was varied by 10 percent (plus or minus) from the target Incromega™/Capmul™/Cremophor™ ratio of 40/25/20 to validate whether the Example 1 formulation is robust in terms of dissolution of $CoQ_{10}$ in water. In addition, other formulations were also included in this mixture design to find the sweet zone, in which all the SEFs can have >75% $CoQ_{10}$ dissolved in de-ionized water within 1 hr. A total of 14 formulations with a duplicate for each were prepared.

Table 2 lists the compositions of these 14 formulations:

TABLE 2

Formulation Compositions in Mixture Design Experiment

| Formulation Code | Incromega™ E3322 | Capmul™ CMC C8 | Cremophor™ EL | CoQ10 | Tocopheryl acetate |
|---|---|---|---|---|---|
| F-1 | 0.39 | 0.28 | 0.18 | 0.10 | 0.05 |
| F-2 | 0.41 | 0.22 | 0.22 | 0.10 | 0.05 |
| F-3 | 0.44 | 0.23 | 0.18 | 0.10 | 0.05 |
| F-4 | 0.36 | 0.28 | 0.22 | 0.10 | 0.05 |
| F-5 | 0.41 | 0.22 | 0.22 | 0.10 | 0.05 |
| F-6 | 0.36 | 0.27 | 0.22 | 0.10 | 0.06 |
| F-7 | 0.85 | 0.00 | 0.00 | 0.10 | 0.06 |
| F-8 | 0.42 | 0.00 | 0.43 | 0.10 | 0.05 |
| F-9 | 0.42 | 0.43 | 0.00 | 0.10 | 0.05 |
| F-10 | 0.28 | 0.28 | 0.28 | 0.10 | 0.05 |
| F-11 | 0.00 | 0.43 | 0.43 | 0.10 | 0.05 |
| F-12 | 0.00 | 0.85 | 0.00 | 0.10 | 0.05 |
| F-13 | 0.00 | 0.00 | 0.85 | 0.10 | 0.05 |
| F-14 | 0.40 | 0.25 | 0.20 | 0.10 | 0.05 |

A small batch of 2 grams was prepared for each formulation by mixing all the components in a 20-ml scintillation vial. All the components, including $CoQ_{10}$ and vitamin E acetate, were admixed at 50° C. for ~2 mins. After mixing, each formulation was filled into a size #2 HPMC hard capsule using a 1-ml pipette, with the target weight of 300 mg/capsule. The capsules were sealed with a mixed solvent of ethanol and de-ionized water at 50/50 by volume.

These LFHCs were measured for their dissolution in de-ionized water using the method of Example 1. Table 3 shows the results.

TABLE 3

Experimental and Predicted Result from DOE Mixture Design

| Formulation code | % dissolved in 1 hr | Predicted from Fit model |
|---|---|---|
| F-1 | 104.2 | 93.5 |
| F-1 | 103.9 | 93.5 |
| F-2 | 100.2 | 104.0 |
| F-2 | 102.7 | 104.0 |
| F-3 | 98.8 | 93.8 |
| F-3 | 101 | 93.8 |
| F-4 | 102.9 | 100.9 |
| F-4 | 103.8 | 100.9 |
| F-5 | 100.5 | 104.0 |
| F-5 | 95.2 | 104.0 |
| F-6 | 101 | 102.8 |
| F-6 | 101.1 | 102.8 |
| F-7 | 5.8 | 5.3 |
| F-7 | 3.5 | 5.3 |
| F-8 | 92.5 | 92.6 |
| F-8 | 93.6 | 92.6 |

TABLE 3-continued

Experimental and Predicted Result from DOE Mixture Design

| Formulation code | % dissolved in 1 hr | Predicted from Fit model |
|---|---|---|
| F-9 | 8.3 | 7.9 |
| F-9 | 1.8 | 7.9 |
| F-10 | 99.7 | 106.9 |
| F-10 | 99.9 | 106.9 |
| F-11 | 9.2 | 7.0 |
| F-11 | 6.7 | 7.0 |
| F-12 | 0 | 0.0 |
| F-12 | 0 | 0.0 |
| F-13 | 10.7 | 8.3 |
| F-13 | 6.4 | 8.3 |
| F-14 | 100.4 | 100.4 |
| F-14 | 100.7 | 100.4 |

Figure 2:
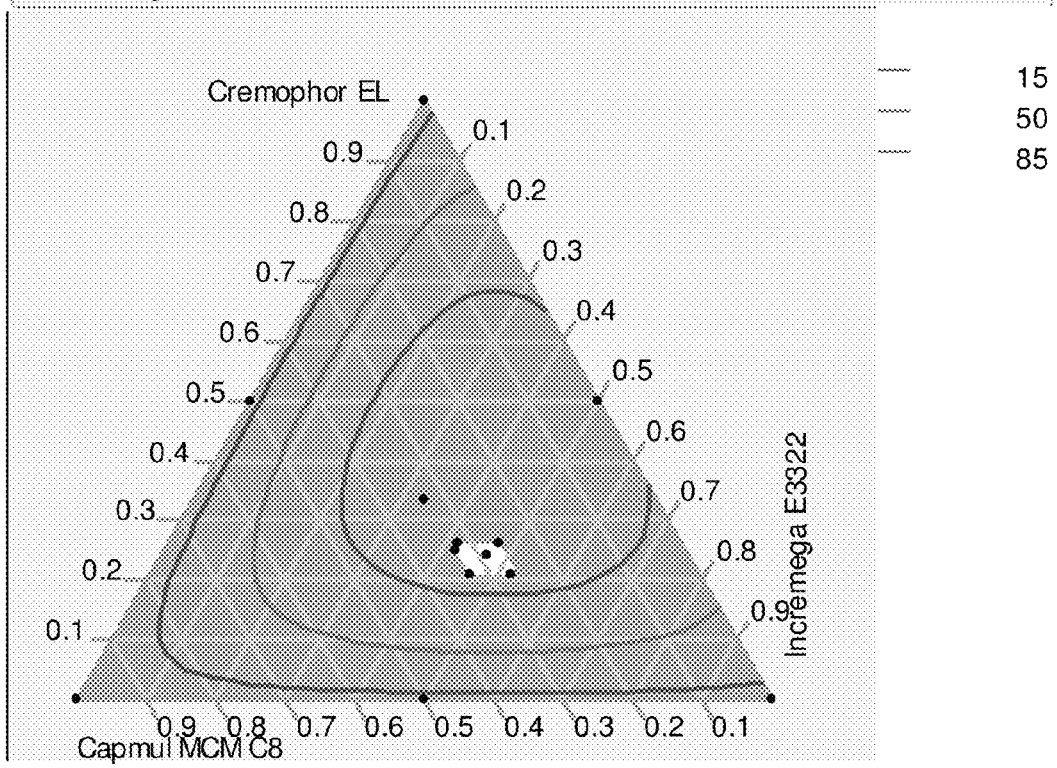
FIG. 2 is a ternary plot showing the effect of varying three constituents of the formulation carrier.

These data were analyzed, using JMP statistical software. The dissolution result was fitted to a prediction model for % of $CoQ_{10}$ dissolved within 1 hr. The predicted profile is shown in the ternary contour plot (FIG. 2). The result shows that those formulations (Formulations 1 through 6), varying 10% (+/−) from the formulation of Example 1 (Formulation 14), all have more than 85% of $CoQ_{10}$ dissolved within 1 hr., which satisfies the USP criterion for water-soluble $CoQ_{10}$. These results also show those formulations that lack Incromega™ or Cremophor™ were not effective. It appears Capmul™ is less essential.

Example 4

Alternative Formulations

A. The procedure in Example 1 is followed, but using 15.00% $CoQ_{10}$, 3.75% vitamin E (d,l-α-tocopheryl acetate) with the weight ratio of Incromega™/Capmul™/Cremophor™ EL or Polysorbate 80™ at 27.08/27.09/27.08. The SEF was filled into a #1 size HPMC hard capsule with target fill weight of 400 mg. Each capsule contains 60 mg of $CoQ_{10}$ and 15 mg of vitamin E acetate (equivalent to 15 IU).

B. The procedure in Example 1 is followed except encapsulating a SEF with soft capsule instead. The SEF in this example comprises 15.00% $CoQ_{10}$, 2.25% vitamin E (d,l-α-tocopheryl acetate) and with the weight ratio of Incromega™/Capmul™/Cremophor™ or Polysorbate 80™ at 27.58/27.57/27.58. The SEF was encapsulated with a soft capsule with the target weight of 667 mg/capsule. Each capsule contains 100 mg of $CoQ_{10}$ and 15 mg of vitamin E acetate (equivalent to 15 IU).

Example 5

Powder Filled Hard Capsules

A. A powder-filled hard capsule is prepared comprising 5.0-8.0% $CoQ_{10}$, 1.0-5.0% vitamin E (d,l-α-tocopheryl acetate), 5.0-10.0% Omega-3 fatty acid ethyl ester, 0.0-10.0% mono-, di-glycerides of caprylic acid, 5.0-10.0% polyoxyl 35 castor oil or Polysorbate 80™ and 40-75.0% of solid which is silicone dioxide, or dibasic calcium phosphate or magnesium aluminum metasilicate or their combination.

All the components, except the solid, are mixed in a mixing vessel at 50° C. for several mins to get a clear, orange-colored solution. The solution is blended with the selected solid to result in freely flowable particulates. The particulates are filled into a #0 size HPMC hard capsule, with a fill weight of 350 to 500 mg. Each capsule contains 18-30 mg of $CoQ_{10}$ and 3.5 to 25 IU of vitamin E.

B. Using the method of paragraph A, a powder-filled hard capsule is prepared comprising 0.25-1.0% vitamin A (retinol palmitate), 0.002-0.010% vitamin D (cholecalciferol), 2.0-10.0% vitamin E (d,l-α-tocopheryl acetate), 0.05-0.20% vitamin K (3-phythylmenadione), 5.0-10.0% Omega-3 fatty acid ethyl ester, 10.0-25.0% polyoxyl 35 castor oil or Polysorbate 80™, and 40.0-75.0% of a solid component which is silicone dioxide or dibasic calcium phosphate or magnesium aluminum metasilicate or their combination.

C. Using the method of paragraph A, a powder-filled hard capsule is prepared comprising 0.25-1.0% vitamin A (retinol palmitate), 2.0-10% vitamin E (d,l-α-tocopheryl acetate), 5.0-10.0% Omega-3 fatty acid ethyl ester, 10.0-25.0% polyoxyl 35 castor oil or Polysorbate 80™, and 40.0-75.0% of a solid component which is silicone dioxide or dibasic calcium phosphate or magnesium aluminum metasilicate or their combination.

D. Using the method of paragraph A, a powder-filled hard capsule is prepared comprising 2.0-10.0% vitamin E (d,l-α-tocopheryl acetate), 0.05-0.20% vitamin K (3-phythylmenadione), 5.0-10.0% Omega-3 fatty acid ethyl ester, 10.0-25.0% polyoxyl 35 castor oil or Polysorbate 80™, and 40.0-75.0% of a solid component which is silicone dioxide or dibasic calcium phosphate or magnesium aluminum metasilicate or their combination.

E. Using the method of paragraph A, a powder-filled hard capsule is prepared comprising 0.25-1.0% vitamin A (retinol palmitate), 0.002-0.010% vitamin D (cholecalciferol), 2.0-10.0% vitamin E (d,l-α-tocopheryl acetate), 5.0-10.0% Omega-3 fatty acid ethyl ester, 10.0-25.0% polyoxyl 35 castor oil or Polysorbate 80™, and 40.0-75.0% of a solid component which is silicone dioxide or dibasic calcium phosphate or magnesium aluminum metasilicate or their combination.

F. Using the method of paragraph A, a powder-filled hard capsule is prepared comprising 1.0 to 5.0% lutein (lutein palmitate), 2.0-10.0% vitamin E (d,l-α-tocopheryl acetate), 5.0-10.0% Omega-3 fatty acid ethyl ester, 10.0-25.0% polyoxyl 35 castor oil or Polysorbate 80™, 0.0-15.0% mono-, di-glycerides of caprylic acid, and 40.0-75.0% of a solid component which is silicone dioxide or dibasic calcium phosphate or magnesium aluminum metasilicate or their combination.

Example 6

Single Layer Tablets

A. The tablet comprises 2.0-5.0% $CoQ_{10}$, 1.0-2.0% vitamin E (d,l-α-tocopheryl acetate), 0.001-0.01% vitamin D (cholecalciferol), 5.0-10.0% Omega-3 fatty acid ethyl ester, 0.0-10.0% mono-, di-glycerides of caprylic acid, 3.0-10.0% polyoxyl 35 castor oil or Polysorbate 80™, 65.0-80.0% of a solid which is silicone dioxide or dibasic calcium phosphate or magnesium aluminum metasilicate or their combination, plus 2.0-5.0% low substituted hydroxypropylcellulose (L-HPC) or other disintegrant, and 0.1-2.0% stearic acid or magnesium stearate. Since the content of vitamin D is very low, it is first dissolved in vitamin E at vitamin D/vitamin E weight ratio for the formulations. Then, $CoQ_{10}$, vitamin E/vitamin D mixture, omega-3 fatty acid ethyl ester, mono-, di-glycerides of caprylic acid, polyoxyl 35 castor oil or Polysorbate 80™, are mixed for several mins at 50° C. to result in a clear, orange-colored solution. The solution is then blended with the solid component to obtain the liquid-loaded particulates, followed by dry-blending with the L-HPC and magnesium stearate to produce homogeneous, yellowish, freely flowable powders.

To form tablets, 953 mg of the powder is compressed under 1 to 2 metric ton force into a single-layer tablet, using 0.70/0.37" oval tooling. Optionally, the tablet can be coated with a clear or colored, water-soluble membrane.

B. Using the method of paragraph A, a tablet is prepared comprising 1.0-3.0% vitamin E (d,l-α-tocopheryl acetate), 0.001-0.10% vitamin D (cholecalciferol), 1.0-2.0% Omega-3 fatty acid ethyl ester, 3.0-10.0% polyoxyl 35 castor oil or Polysorbate 80™, 10.0-20.0% of a solid component which is silicone dioxide or dibasic calcium phosphate or magnesium aluminum metasilicate or their combination, 40.0-60.0% calcium carbonate, 10.0-30.0% micro-crystalline cellulose, 2.0-5.0% low substituted hydroxypropylcellulose (L-HPC) or other disintegrant, and 0.5-1.0% magnesium stearate. The target tablet weight is 960 mg instead.

Example 7

Additional Single Layer Tablet Forms

A. Twelve grams of $CoQ_{10}$ and 12 g of Pluronic® F127 are dissolved in 50 ml of isopropanol alcohol (IPA) at ~60° C. The solution is then charged onto 65.5 g of calcium hydrogen phosphate powder (Fujicalin® SG) and blended well. IPA is removed from the mixture by evaporation in a fume hood overnight. The $CoQ_{10}$-loaded powder is dry-blended for ~1 hour with 5 g of croscarmellose (Ac-Di-Sol), 5 g of hydroxypropylcellulose (Klucel™ EF), and 0.5 g of mg stearate. Five hundred mg of the blend are compressed into a tablet using a compressing press. Each tablet comprises 30 mg of $CoQ_{10}$.

B. The procedure in paragraph A is followed, but using poly(vinyl acetate polymer-co-vinylpyrrolidone) (VA 64) instead of Pluronic® F127.

C. The procedure in paragraph A is followed, but substituting hydroxypropylmethyl cellulose (HPMC E3 or HPMC K3) for Pluronic® 127. The HPMC is first solubilized in a mixed solvent of water and IPA at a weight ratio of 15/85.

D. The procedure in paragraph A is followed, but instead of CoQ10, various forms and precursors of poorly water soluble vitamins A, D, and K are solubilized with Pluronic® F127 in an alcohol. In addition to the pharmaceutical excipients listed in paragraph A, the tablet can comprise various forms of Vitamin B1 (riboflavin), B2 (thiamine), B3 (niacin), B5 (pantothenic acid), B6, B8 (biotin), B9 (folic acid), B12, Vitamin C, and commercially consumed mineral supplement forms of calcium, phosphorus, magnesium, iron, zinc, copper, manganese, selenium, chromium, molybdenum, and iodine. Each tablet contains 5,000 I.U. units of Vitamin A, 400 I.U. units of Vitamin D, 30 I.U. of Vitamin E, 1.5 mg of Vitamin B1, 1.7 mg of Vitamin B2, mg of Vitamin B3, 10 mg of Vitamin B5, 2 mg of Vitamin B6, 6 ug of Vitamin B12, 0.4 mg of Vitamin B9, 0.3 mg of Vitamin B8, 60 mg of Vitamin C, 1,000 mg of calcium, 1,000 mg of phosphorus, 400 mg of magnesium, 18 mg of iron, 15 mg of zinc, 150 ug of iodine, 2 mg of copper, 2 mg of manganese, 70 ug of selenium, 120 ug of chromium, and 75 ug of molybdenum.

Example 8

Encapsulated Solid Formulation

A. Six grams of $CoQ_{10}$, 8.5 g of Vitamin E TPGS and 25.5 g of omega-3 fatty acid ethyl ester (Incromega™ E) are mixed for ~10 mins at ~60° C. to result in a $CoQ_{10}$ self-emulsifying formulation (SEF). Then, 60 g of Fujicalin® SG are blended with the SEF to get a SEF-loaded powder. Finally, 500 mg of the SEF-loaded powder are filled into an elongated 0 size hydroxypropylmethylcellulose capsule (V-Cap). Each capsule contains 30 mg of $CoQ_{10}$.

The procedure of paragraph A is followed, but employing 15 wt % of $CoQ_{10}$, 42.5% of Cremophor™ EL and 42.5% of an acetated monoglyceride (Myvacet™ 9-34).

The procedure of paragraph A is followed, but employing 15 wt % of $CoQ_{10}$, 21% of Cremophor™ EL and 64% of a medium chain mono-, diglyceride (Capmul™ MCM).

The procedure of paragraph A is followed, but employing 15 wt % of $CoQ_{10}$, 21% of Cremophor™ EL and 64% of glyceryl monocaprate (Capmul™ MCM C10).

The procedure of paragraph A is followed, but employing 15 wt % of $CoQ_{10}$, 21% of Cremophor™ EL and 64% of glyceryl monocaprylate (Capmul™ MCM C8).

The procedure of paragraph A is followed, but employing 15 wt % of $CoQ_{10}$, 21% of Cremophor™ EL and 64% of propylene glycol caprylate (Capmul™ PG-8).

The procedure of paragraph A is followed, but employing 15 wt % of $CoQ_{10}$, 21% of Vitamin E TPGS and 64% of a medium chain mono-, diglyceride (Capmul™ MCM).

The procedure of paragraph A is followed, but employing precursors of poorly water soluble vitamins A, D, and K which are solubilized in a SEF comprising Vitamin E TPGS and omega-3 fatty acid ethyl ester (Incromega™ E). In addition to the pharmaceutical excipients listed in paragraph A, the tablet can comprise various forms of Vitamin B1 (riboflavin), B2 (thiamine), B3 (niacin), B5 (pantothenic acid), B6, B8 (biotin), B9 (folic acid), B12, Vitamin C, and commercially consumed mineral supplement forms of calcium, phosphorus, magnesium, iron, zinc, copper, manganese, selenium, chromium, molybdenum, and iodine. Each tablet contains 5,000 I.U. units of Vitamin A, 400 I.U. units of Vitamin D, 30 I.U. of Vitamin E, 1.5 mg of Vitamin B1, 1.7 mg of Vitamin B2, 20 mg of Vitamin B3, 10 mg of Vitamin B5, 2 mg of Vitamin B6, 6 ug of Vitamin B12, 0.4 mg of Vitamin B9, 0.3 mg of Vitamin B8, 60 mg of Vitamin C, 1,000 mg of calcium, 1,000 mg of phosphorus, 400 mg of magnesium, 18 mg of iron, 15 mg of zinc, 150 ug of iodine, 2 mg of copper, 2 mg of manganese, 70 ug of selenium, 120 ug of chromium, and 75 ug of molybdenum.

Example 9

Alternative Solid Formulation

In this example, CoQ10, Vitamin E TPGS, Omega-3 fatty acid ethyl ester (Incromega™ E), and the poorly water soluble Vitamins A, D and K are mixed for ~10 mins at ~60° C. to result in a self-emulsifying formulation (SEF). Then, Fujicalin® SG is blended with the SEF to get a SEF-loaded powder. Finally, 500 mg of the SEF-loaded powder are filled into an elongated 0 size HPMC capsule (V-Cap or Qualicap).

Example 10

Liquid Formulation

In this example, 6 g of $CoQ_{10}$, 8.5 g of Vitamin E TPGS and 25.5 g of omega-3 fatty acid ethyl ester (Incromega™ E) are mixed for ~10 mins at ~60° C. to result in a $CoQ_{10}$ self-emulsifying formulation (SEF). Then, the SEF is mixed with water and a flavor to get a drink concentrate with $CoQ_{10}$ concentration 60 mg/ml.

Example 11

Bilayer Tablets

A. A bi-layer-layer tablet is prepared as follows. The first layer comprises $CoQ_{10}$ and the oil-soluble vitamins, while the other layer comprises the water-soluble vitamins and minerals.

The first layer comprises 1.0-5.0% $CoQ_{10}$, 1.0-5.0% vitamin E (d,l-α-tocopheryl acetate), 0.001-0.01% vitamin D (cholecalciferol), 0.10-0.30% vitamin A (retinol palmitate), 0.001-0.005% vitamin K (phytonadione), 5.0-10.0% omega-3 fatty acid ethyl ester, 0.0-10.0% mono-, di-glycerides of caprylic acid, 3.0-10.0% polyoxyl 35 castor oil or Polysorbate 80™, 60.0-80.0% of a solid component which is silicone dioxide, or dibasic calcium phosphate or magnesium aluminum metasilicate or their combination, plus 5.0-10.0% low substituted hydroxypropylcellulose (L-HPC) or other disintegrant, and 0.5-1.0% magnesium stearate.

The second layer comprises ascorbic acid, calcium D-pantothenate, folic acid, niacinamide, pyridoxine hydrochloride, riboflavin, thiamine mononitrate, cyanocobalamin, copper gluconate, zinc oxide, ferrous fumarate, magnesium phosphate, manganese sulfate, potassium iodide, sodium molybdate, sodium selenite, biotin, potassium chloride, chromium chloride, boron amino acid chelate, nickel sulfate, silicon dioxide, stannous chloride, sodium metavanadate, a disintegrate, a lubricant, and a binder (optional).

First, $CoQ_{10}$, vitamin A, vitamin D, vitamin E, vitamin K, omega-3 fatty acid ethyl ester, mono-, di-glycerides of caprylic acid, polyoxyl 35 castor oil or Polysorbate 80™ are mixed for several mins at 50° C. to result in a clear, orange-colored solution. The solution was blended with the solid component to obtain liquid-loaded particulates. These were dry-blended with L-HPC and magnesium stearate to produce homogeneous, yellowish, freely flowable powders.

All the components in the second layer are dry-blended or granulated in a mixing vessel.

The first-layer powders and the second-layer dry-blend or granulates are compressed into the bi-layer tablet under 1 to 2 metric ton of force, using 0.70×0.37" oval toolings, with the target weight for the first and second layer being 502 mg and 431 mg, respectively.

B. The preparation is as in paragraph A, except the first layer comprises 2.0-5.0% vitamin E (d,l-α-tocopheryl acetate), 0.001-0.01% vitamin D (cholecalciferol), 0.10-0.3% vitamin A (retinol palmitate), 0.001-0.005% vitamin K (phytonadione), 5.0-10.0% omega-3 fatty acid ethyl ester, 0.0-10.0% mono-, di-glycerides of caprylic acid, 3.0-10.0% polyoxyl 35 castor oil or Polysorbate 80™, and 60.0-80.0% of solid component, plus 5.0-10.0% low substituted hydroxypropylcellulose (L-HPC) or other disintegrant, and 0.5-1.0% magnesium stearate.

C. The procedure in paragraph A is followed except the first layer comprises 2.0-5.0% vitamin E (d,l-α-tocopheryl acetate), 0.001-0.01% vitamin D (cholecalciferol), 0.10-0.30% vitamin A (retinol palmitate), 0.001-0.005% vitamin K (phytonadione), 0.01-0.05% lycopene, 0.01-0.10% lutein, 5.0-10.0% omega-3 fatty acid ethyl ester, 0.0-10.0% mono-, di-glycerides of caprylic acid, 3.0-10.0% polyoxyl 35 castor oil or Polysorbate 80™, 60.0-80.0% of the solid component, plus 5.0-10.0% low substituted hydroxypropylcellulose (L-HPC) or other disintegrant, and 0.5-1.0% magnesium stearate. In addition, 0.10 to 0.2 mg per tablet of lycopence can be also added the second layer.

D. To prepare an orally dispensable tablet formulation for pediatric use, the procedure of paragraph A is followed except the first layer comprises 2.0-5.0% vitamin E (d,l-α-tocopheryl acetate), 0.001-0.01% vitamin D (cholecalciferol), 0.10-0.30% vitamin A (retinol palmitate), 0.001-0.005% vitamin K (phytonadione), 10.0-15.0% polyoxyl 35 castor oil or Polysorbate 80™, 40.0-60.0% of a solid component which is silicone dioxide, or dibasic calcium phosphate or magnesium aluminum metasilicate or their combination, 20.0-35.0% microcrystalline cellulose, plus 5.0-10.0% low substituted hydroxypropylcellulose (L-HPC) or other disintegrant, 0.5-2.0% sucralose, 1.0-3.0% cherry flavor and 0.5-1.0% magnesium stearate.

The invention claimed is:

1. An oral dosage form which is a self-emulsifying formulation (SEF) comprising an effective amount of coenzyme $Q_{10}$ ($CoQ_{10}$) and a carrier
   a) wherein the carrier comprises
      i) a polyoxyl castor oil;
      ii) omega-3 fatty acids or omega-3 fatty acid ethyl esters or mixtures thereof;
      iii) tocopherol; and
      iv) fatty acid mono- or di-glycerides; or
   b) an SEF wherein the carrier is as set forth in a) sorbed onto porous solid particulates;
   wherein said SEF accommodates >100 mg/ml $CoQ_{10}$.

2. The dosage form of claim 1, wherein said $CoQ_{10}$ is present in the SEF at a concentration of more than 100 mg/ml.

3. The dosage form of claim 1 which is contained in a two-piece hard or soft capsule.

4. A process for preparing the dosage form of claim 1 which comprises
   i) dissolving coenzyme $Q_{10}$ ($CoQ_{10}$) into the carrier of claim 1 to obtain a self-emulsifying formulation (SEF) at an elevated first temperature,
   ii) cooling the SEF of i) or
   iii) sorbing the SEF of i) into porous particulates, and cooling the particulates.

5. The process of claim 4 which further includes encapsulating the cooled SEF prepared in step ii) or the particulates prepared in step iii) into a two-piece hard capsule, or
   which further includes blending and granulating the porous particulates prepared in step iii) with water-soluble vitamins or minerals or other pharmaceutical excipients to obtain granules and compressing the granules into a tablet.

6. The dosage form of claim 1 wherein said SEF is sorbed onto porous solid particulates.

7. The dosage form of claim 6, wherein said porous solid particulates are of calcium hydrogen phosphate and/or aluminometallosilicate and/or silicon dioxide.

8. The dosage form of claim 7, wherein the said porous solid particulates are crystalline and possess pore sizes less than 0.1 μm; a specific surface area of >30 m$^2$/g, and sorb at least 0.5 ml/g of the SEF while maintaining flowability.

* * * * *